United States Patent
Teague et al.

(10) Patent No.: US 7,824,415 B2
(45) Date of Patent: Nov. 2, 2010

(54) ATRAUMATIC MEDICAL DEVICE

(75) Inventors: James A. Teague, Spencer, IN (US); Mohamed Fazni Abdulaziz, Bloomington, IN (US); Juli L. Curtis, Bloomington, IN (US); Aaron J. Bultman, Bloomington, IN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 929 days.

(21) Appl. No.: 10/941,419

(22) Filed: Sep. 15, 2004

(65) Prior Publication Data

US 2006/0058813 A1 Mar. 16, 2006

(51) Int. Cl.
*A61B 17/22* (2006.01)

(52) U.S. Cl. .................................................. 606/127

(58) Field of Classification Search ............... 606/106, 606/108, 127, 128, 200, 159; 128/830, 831; 135/29, 30
See application file for complete search history.

(56) References Cited

U.S. PATENT DOCUMENTS

| | | | |
|---|---|---|---|
| 4,493,320 A * | 1/1985 | Treat | 606/47 |
| 4,590,938 A | 5/1986 | Segura et al. | 606/127 |
| 5,057,114 A | 10/1991 | Wittich et al. | 606/127 |
| 5,064,428 A | 11/1991 | Cope et al. | 606/127 |
| 5,171,233 A * | 12/1992 | Amplatz et al. | 604/540 |
| 5,176,688 A | 1/1993 | Narayan et al. | 606/128 |
| 5,374,273 A | 12/1994 | Nakao et al. | 606/127 |
| 5,746,767 A * | 5/1998 | Smith | 606/200 |
| 5,957,932 A | 9/1999 | Bates et al. | 606/127 |
| 5,989,266 A * | 11/1999 | Foster | 606/127 |
| 6,059,793 A | 5/2000 | Pagedas | 606/114 |
| 6,083,220 A | 7/2000 | Guglielmi et al. | 606/32 |
| 6,096,053 A | 8/2000 | Bates | 606/159 |
| 6,152,922 A * | 11/2000 | Ouchi | 606/47 |
| 6,152,932 A | 11/2000 | Ternström | 606/114 |
| 6,159,220 A | 12/2000 | Gobron et al. | 606/127 |
| 6,187,017 B1 | 2/2001 | Gregory, Jr. | 606/127 |
| 6,224,612 B1 * | 5/2001 | Bates et al. | 606/114 |
| 6,264,664 B1 | 7/2001 | Avellanet | 606/128 |

(Continued)

FOREIGN PATENT DOCUMENTS

WO        WO 93/15671        8/1993

(Continued)

OTHER PUBLICATIONS

International Search Report for International Application No. PCT/US2005/030623, dated Dec. 7, 2005.

(Continued)

*Primary Examiner*—(Jackie) Tan-Uyen T Ho
*Assistant Examiner*—Dianne Dornbusch
(74) *Attorney, Agent, or Firm*—Finnegan, Henderson, Farabow, Garrett & Dunner, L.L.P.

(57) ABSTRACT

A medical device, and related method, for manipulating material, such as calculi, within a patient's body includes a handle, a sheath, a retrieval basket, and a retainer coupled to the distal end of the retrieval basket. The retrieval basket includes a plurality of legs, each of which includes an intermediate portion located at the distal end of the retrieval basket. The retainer secures at least the intermediate portion of one of the plurality of legs to the intermediate portion of another of the plurality of legs.

17 Claims, 16 Drawing Sheets

U.S. PATENT DOCUMENTS

| | | | |
|---|---|---|---|
| 6,302,127 B1 * | 10/2001 | Gayton | 135/124 |
| 6,302,895 B1 | 10/2001 | Gobron et al. | 606/127 |
| 6,319,262 B1 * | 11/2001 | Bates et al. | 606/127 |
| 6,673,080 B2 | 1/2004 | Reynolds et al. | 606/127 |
| 7,101,379 B2 * | 9/2006 | Gregory et al. | 606/127 |
| 7,678,119 B2 * | 3/2010 | Little et al. | 606/128 |
| 2001/0001315 A1 * | 5/2001 | Bates et al. | 606/114 |
| 2003/0088254 A1 * | 5/2003 | Gregory et al. | 606/127 |
| 2003/0225419 A1 * | 12/2003 | Lippitt et al. | 606/127 |
| 2004/0116941 A1 | 6/2004 | Reynolds et al. | 606/128 |
| 2004/0122445 A1 | 6/2004 | Butler et al. | |
| 2004/0138677 A1 * | 7/2004 | Little et al. | 606/127 |

FOREIGN PATENT DOCUMENTS

| | | |
|---|---|---|
| WO | WO 99/48429 | 12/1999 |
| WO | WO 00/71036 A2 | 11/2000 |
| WO | WO 01/10290 A3 | 2/2001 |

OTHER PUBLICATIONS

The Written Opinion of the International Searching Authority dated Dec. 7, 2005.

International Preliminary Report on Patentability for International Application No. PCT/US2005/030623, dated Mar. 29, 2007.

* cited by examiner

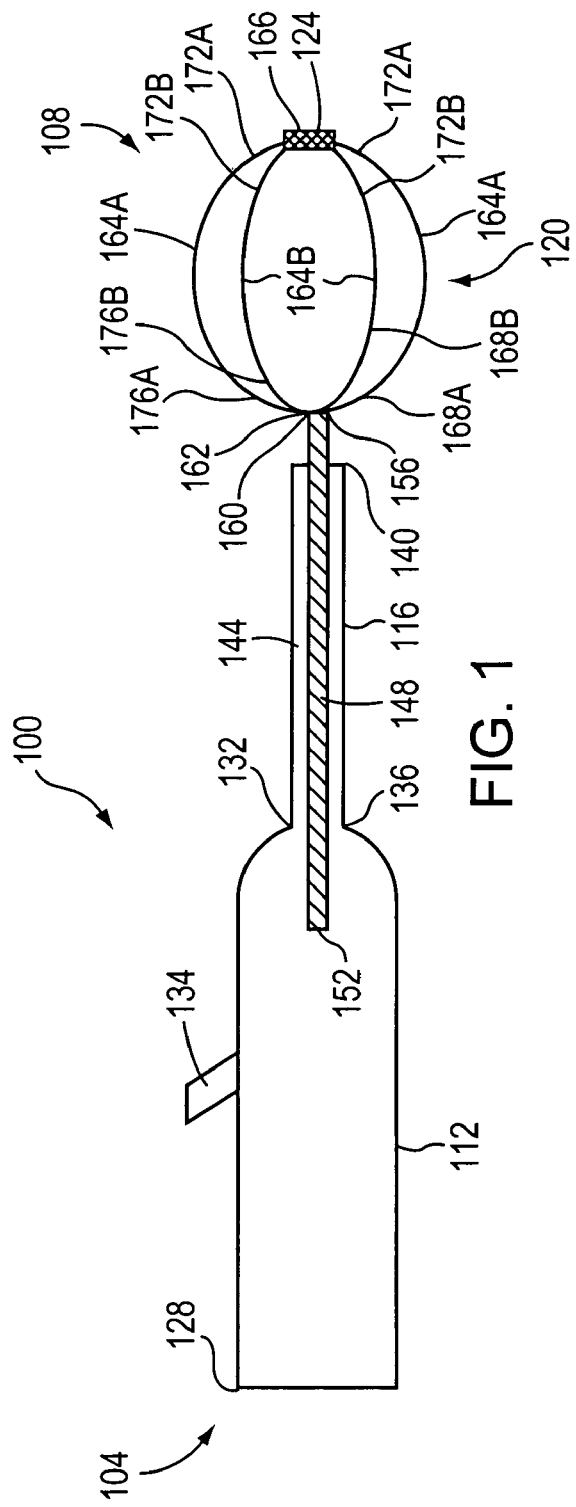
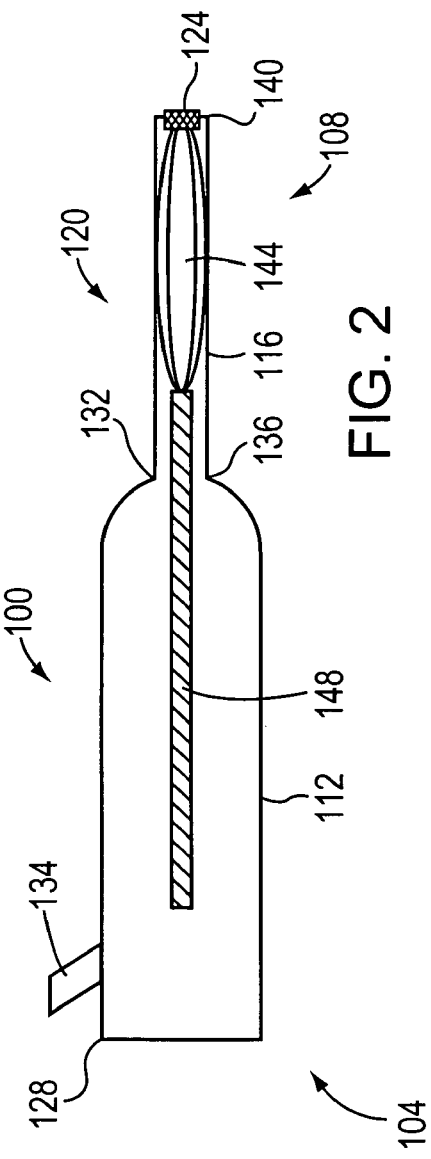

ATRAUMATIC MEDICAL DEVICE

TECHNICAL FIELD

The invention generally relates to medical devices for retrieving, trapping, and sweeping material within a patient's body. More particularly, the invention relates to medical devices that have atraumatic distal ends. The atraumatic distal ends minimize the chance of damaging surrounding tissues during the use of the devices and enhance the ability of the devices to manipulate material (e.g., calculi) disposed or lodged in areas that are difficult to access in the body.

BACKGROUND

A medical device can be used to retrieve calculi from a body. One type of known medical device has a sheath and a retrieval basket that is moveable in and out of the sheath. Typically, the retrieval basket is constructed by joining multiple legs together, both at a base of the retrieval basket and at a distal end of the retrieval basket, such that a "cage" is formed. At the distal end of the retrieval basket, the individual legs are joined by, for example, soldering or welding. A protruding tip at the distal end of the retrieval basket results.

In a clinical application, this protrusion or outward projection at the distal end of the retrieval basket may poke tissue and cause tissue trauma. Further, the protruding tip may hinder the ability to access calculi located within some areas of the body.

Improved devices and methods for manipulating material within a body are, therefore, needed.

SUMMARY OF THE INVENTION

The invention generally relates to devices and methods for the manipulation of material within the body of a patient. The devices and methods allow access to, and/or intimate contact with, the areas of the body where the material to be manipulated resides. The devices and methods also generally avoid damaging the lining of the body tract in those areas. One embodiment of a device according to the invention includes a retrieval basket, with a substantially atraumatic distal end, that is capable of sweeping, capturing and releasing biological and/or foreign material (e.g., calculi). The retrieval basket may be used, for example, as a sweeper, a urological retrieval basket, as an endoscopic retrieval basket, or as a lithotripsy-assist device.

In one aspect of the invention, a medical device includes a handle, a sheath joined to the handle, a retrieval basket, and a retainer coupled to the distal end of the retrieval basket. The sheath includes a lumen and the retrieval basket includes a proximal end, a distal end, and a plurality of legs. Each of the plurality of legs includes a first end, a second end, and an intermediate portion. The first and second ends of the plurality of legs are located at the proximal end of the retrieval basket and the intermediate portion of each of the plurality of legs is located between the first and second ends of the leg and at the distal end of the retrieval basket. The retainer secures at least the intermediate portion of one of the plurality of legs to the intermediate portion of another of the plurality of legs. The intermediate portions of the legs may cross one another, or they may be side-by-side, while being secured together by the retainer. The retrieval basket achieves a collapsed position when restrained in the lumen of the sheath and an expanded position when unrestrained by the lumen of the sheath.

Various embodiments of this aspect of the invention include the following features. The retainer may include at least two bands, which, in one embodiment, are made of a heat shrink material. In another embodiment, the retainer includes a plurality of tubes and each tube includes a first end, a second end, and a hollow passageway extending from the first end to the second end. Each of the plurality of tubes may also include an intermediate section and at least the intermediate section of one of the plurality of tubes may intersect the intermediate section of another of the plurality of tubes. In one embodiment, at least the hollow passageway of one of the plurality of tubes is in fluid communication with the hollow passageway of another of the plurality of tubes. The plurality of tubes may be made of a heat shrink material.

In yet another embodiment, the retainer includes a knob. The knob may be injection molded to the distal end of the retrieval basket. Alternatively, the knob may be heat shrunk to the distal end of the retrieval basket. In yet another embodiment, the knob includes an adhesive. In still another embodiment, the retainer includes a first member, which includes a plurality of risers, and a second member. In one embodiment, the first member is coupled to the second member.

In further embodiments, the retainer includes a lumen and a plurality of openings in fluid communication with the lumen. The retainer may be arch-shaped or, alternatively, cylindrical-shaped. Additionally, in one embodiment, the intermediate portion of at least one of the plurality of legs of the retrieval basket includes a connecting surface. The connecting surface may include at least one notch.

In another aspect, the invention relates to a method of manipulating a material within a body. The method includes inserting a medical device, as described above, into the body, positioning the retrieval basket proximate to the material to be manipulated with the retrieval basket in the expanded position, capturing or sweeping the material with the retrieval basket, and withdrawing the retrieval basket from the body to remove or dislodge the material from or within the body. In one embodiment of this aspect of the invention, the material includes a calculus.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a schematic side view of a medical device with a retrieval basket in an expanded position according to an illustrative embodiment of the invention.

FIG. 2 is a schematic side view of the illustrative medical device of FIG. 1 with the retrieval basket in a collapsed position.

DESCRIPTION

Figure 3:
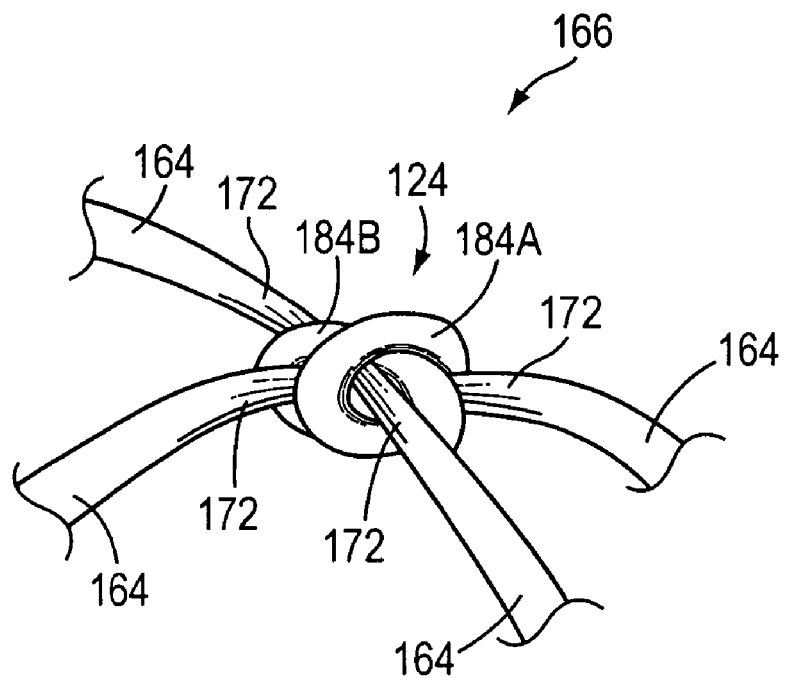
FIG. 3 is a perspective view of a distal end of a retrieval basket according to an illustrative embodiment of the invention.

In general, the invention pertains to devices and methods relating to the manipulation of material within the body of a patient. The medical device of the present invention may be used to trap, sweep, and/or retrieve materials within the body of a patient.

FIG. 1 depicts a medical device 100 according to an illustrative embodiment of the invention. As shown, the medical device 100 includes a proximal end 104 (i.e., an end that is closest to an operator of the medical device 100), an opposite distal end 108, a handle 112, a sheath 116, a retrieval basket 120, and a retainer 124. The handle 112 is located at the proximal end 104 of the medical device 100 and has, itself, a proximal end 128 and a distal end 132. An actuating mechanism 134 is positioned on the handle 112. For its part, the sheath 116 has a proximal end 136, a distal end 140, and a longitudinally disposed lumen 144 that extends from the proximal end 136 to the distal end 140. An elongated member 148, such as, for example, a tube, a sheath, a cable, a coil, a shaft, a guidewire, or a mandril wire, axially extends in the lumen 144 of the sheath 116. The elongated member 148 has a proximal end 152 and a distal end 156 that couples to a base 160 of the retrieval basket 120. In some embodiments, the elongated member 148 also has a longitudinally disposed lumen (not shown). The lumen of the elongated member 148 may be adapted to accommodate, for example, an optical fiber for visualization, and/or a laser fiber for stone destruction. In one embodiment, the proximal end 136 of the sheath 116 attaches to the distal end 132 of the handle 112 and the proximal end 152 of the elongated member 148 couples to the actuating mechanism 134 of the handle 112. Alternatively, the proximal end 136 of the sheath 116 couples to the actuating mechanism 134 of the handle 112 and the proximal end 152 of the elongated member 148 attaches to the distal end 132 of the handle 112.

Referring still to FIG. 1, the base 160 of the retrieval basket 120 is located at a proximal end 162 of the retrieval basket 120. A distal end 166 of the retrieval basket 120 is located opposite to the proximal end 162, i.e., the distal end 166 is further from the operator than the proximal end 162. In general, a plurality of legs 164 form the retrieval basket 120. For example, in one embodiment, the retrieval basket 120 may have two legs 164, such as a first leg 164A and a second leg 164B, as shown. The legs 164 may be made from a variety of resilient materials, such as, for example, metal or metal alloys (e.g., nickel-titanium, stainless steel, etc.). Alternatively, the legs 164 may be made from plastic or a combination of metal, metal alloys, and plastic. As shown, in one embodiment, each of the legs 164A, 164B has a first end 168, an intermediate portion 172, and a second end 176. Each of the legs 164A, 164B forms a loop. Accordingly, both the first ends 168 and the second ends 176 of the legs 164 are located at the base 160 of the retrieval basket 120 (i.e., at the proximal end 162 of the retrieval basket 120) and couple to each other or to the distal end 156 of the elongated member 148. The intermediate portions 172 of the legs 164 are located between the first ends 168 and the second ends 176 of the legs 164. Accordingly, the distal end 166 of the retrieval basket 120 includes at least a portion of the intermediate portions 172 of the legs 164. As explained in greater detail below, the retainer 124 is located at the distal end 166 of the retrieval basket 120 and secures the intermediate portion 172A of the leg 164A to the intermediate portion 172B of the leg 164B.

Operation of the actuating mechanism 134 by an operator (e.g., a physician) causes the retrieval basket 120 to achieve a collapsed position, as shown in FIG. 2, or an expanded position, as shown in FIG. 1. Referring to FIG. 2, in one embodiment, the retrieval basket 120 is restrained, in the collapsed position, within the lumen 144 of the sheath 116. The retrieval basket 120 may be reciprocally moved between the collapsed position shown in FIG. 2 to the expanded position shown in FIG. 1. In the expanded position shown in FIG. 1, the legs 164 of the retrieval basket 120 extend beyond the distal end 140 of the sheath 116.

In the illustrative embodiments of FIGS. 1 and 2, the retrieval basket 120 alternates between the collapsed position illustrated in FIG. 2 and the expanded position illustrated in FIG. 1 by slideable movement of the elongated member 148 in the lumen 144 of the sheath 116. For example, by proximally withdrawing the actuating mechanism 134, the operator withdraws the elongated member 148 and restrains the retrieval basket 120 in the lumen 144 of the sheath 116. The retrieval basket 120 thereby achieves the collapsed position. By distally advancing the actuating mechanism 134, the operator advances the elongated member 148 and positions the retrieval basket 120 beyond the distal end 140 of the sheath 116. The retrieval basket 120 opens and expands to achieve the expanded position.

Alternatively, according to another embodiment of the invention (not shown), an operator moves the retrieval basket 120 between the collapsed and expanded positions by distally advancing or proximally withdrawing the sheath 116 over a stationary elongated member 148 and the retrieval basket 120. For example, by distally advancing the actuating mechanism 134, the operator advances the moveable sheath 116 over the stationary elongated member 148 and the retrieval basket 120, thereby collapsing the retrieval basket 120 within the lumen 144 of the sheath 116. By proximally withdrawing the actuating mechanism 134, the operator withdraws the moveable sheath 116 and exposes the retrieval basket 120 beyond the distal end 140 of the sheath 116. The retrieval basket 120 opens and expands to achieve the expanded position.

In general, both types of elongated member/sheath movement configurations and related handle mechanisms are known, and can be seen in existing product designs available from, for example, Boston Scientific Corporation (Natick, Mass.).

FIG. 2 depicts the medical device 100 with the retrieval basket 120 in a collapsed position according to an illustrative embodiment of the invention. In this embodiment, while the retrieval basket 120 is collapsed and restrained within the lumen 144 of the sheath 116, an operator inserts the distal end 140 of the sheath 116 into the body of a patient. The operator advances the distal end 140 of the sheath 116 to an anatomical site where the material to be manipulated is located (e.g., a calculus in the ureter). By placing the retrieval basket 120 in its open/expanded position, as illustrated in FIG. 1, the operator positions the retrieval basket 120 adjacent the material to be retrieved and maneuvers the retrieval basket 120 to entrap or capture the material within the retrieval basket 120. By proximally withdrawing the elongated member 148 or, alternatively, by distally advancing the sheath 116, the operator positions the proximal portion of the retrieval basket 120 within the lumen 144 of the sheath 116. Consequently, the legs 164 of the retrieval basket 120 close around the material and secure the material within the retrieval basket 120. According to one embodiment of the invention, the sheath 116, the retrieval basket 120, and the captured material are withdrawn from the patient's body. In an alternative embodiment, the captured material is fragmented by a lithotriptor, such as, for example, a laser or a mechanical lithotriptor. The sheath 116, the retrieval basket 120, and the captured material are then removed from the patient's body. Alternatively, the operator may also use the medical device 100 to dislodge or sweep material from a first anatomical site, for example, a tortuous body tract, to a second anatomical site where the material may be more easily removed or destroyed.

Referring again to FIG. 1, the retainer 124 is positioned at the distal end 166 of the retrieval basket 120. The general purpose of the retainer 124 is to join and secure together the intermediate portions 172 of the legs 164 at the distal end 166 of the retrieval basket 120. In one embodiment, the intermediate portions 172 of the legs 164 cross one another at the distal end 166 of the retrieval basket 120, where they are secured by the retainer 124. In another embodiment, the retainer 124 holds the intermediate portions 172 of the legs 164 side-by-side at the distal end 166 of the retrieval basket 120. In general, the retainer 124 has an atraumatic structure. Specifically, the retainer 124 is devoid of any outward projections or protrusions that might cause injury or trauma to tissue. There is, therefore, no impediment to contacting the distal end 166 of the retrieval basket 120 directly and intimately with tissue.

Figure 4:
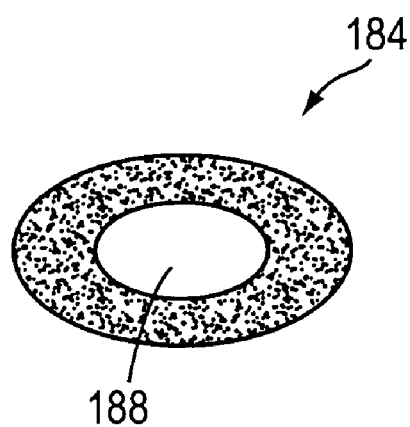
FIG. 4 is a plan view of a retainer according to an illustrative embodiment of the invention.

FIG. 3 depicts a perspective view of a distal end 166 of a retrieval basket 120, including the retainer 124, according to an illustrative embodiment of the invention. As shown, in the illustrative embodiment, the retainer 124 includes two bands 184A, 184B. Alternatively, the retainer 124 may include one band 184 or any number of bands 184. As illustrated in FIG. 4, in one embodiment, the band 184 is substantially elliptical in shape, enclosing a lumen 188. Alternatively, the band 184 may assume other shapes which enclose a lumen 188.

In one embodiment, referring again to FIG. 3, the bands 184 are constructed of a heat shrink material, such as, for example, polytetrafluoroethylene (PTFE) or a cross-linked polyolefin. The intermediate portions 172 of the legs 164 pass through the lumen 188 of one or more bands 184. As such, the bands 184 join and secure together the intermediate portions 172 of the legs 164 at the distal end 166 of the retrieval basket 120.

Figure 5:
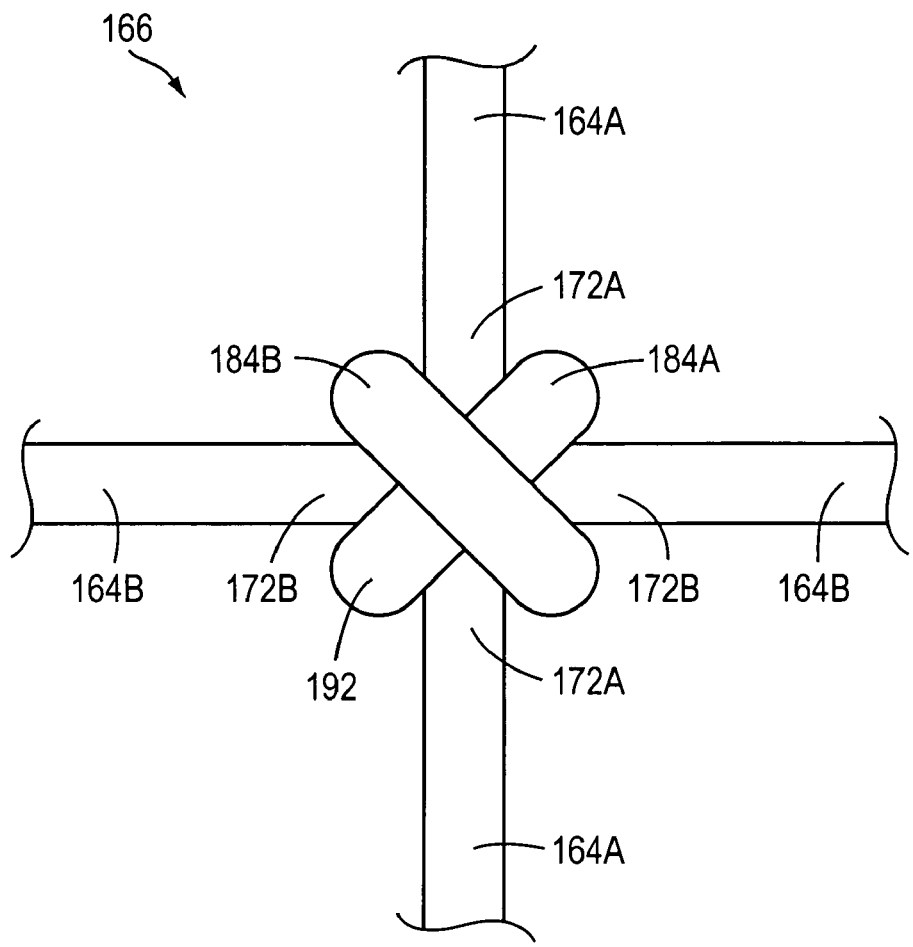
FIG. 5 is an end view of the illustrative distal end of the retrieval basket of FIG. 3.

In one feature of this embodiment of the invention, referring now to FIG. 5, the intermediate portions 172A, 172B of the legs 164A, 164B cross one another at a crossing point 192 at the distal end 166 of the retrieval basket 120. In this embodiment, for example, the bands 184A, 184B are offset by approximately 90 degrees from one another. Each band 184A, 184B encircles a portion of the intermediate portion 172 of each leg 164, and bands 184A, 184B together form an X-shape. Accordingly, the intermediate portion 172 of each leg 164 passes through the lumen 188 of each band 184.

Figure 6:
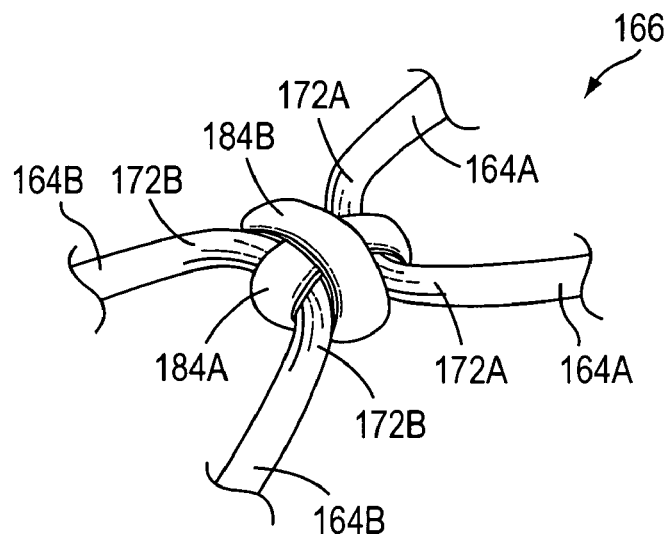
FIG. 6 is a perspective view of a distal end of a retrieval basket according to another illustrative embodiment of the invention.

In another embodiment, referring now to FIG. 6, a portion of the intermediate portions 172A, 172B of the legs 164A, 164B are side-by-side, but do not cross one another, at the distal end 166 of the retrieval basket 120. In this embodiment, for example, the bands 184A, 184B are offset by approximately 90 degrees from one another, and together form an X-shape. Only the first band 184A encircles a portion of the intermediate portion 172 of the legs 164A and 164B. Accordingly, the intermediate portion 172 of each leg 164A, 164B passes through the lumen 188A of the first band 184A. The second band 184B encircles the first band 184A, but not the intermediate portion 172 of any of the legs 164A, 164B. The intermediate portions 172 of the legs 164 do not cross one another and, therefore, the distal end 166 of the retrieval basket 120 illustrated in FIG. 6 has a lower profile than the distal end 166 of the retrieval basket 120 illustrated in FIG. 5. In another embodiment, the distal end 166 of the retrieval basket 120 includes only the band 184A.

Figure 7:
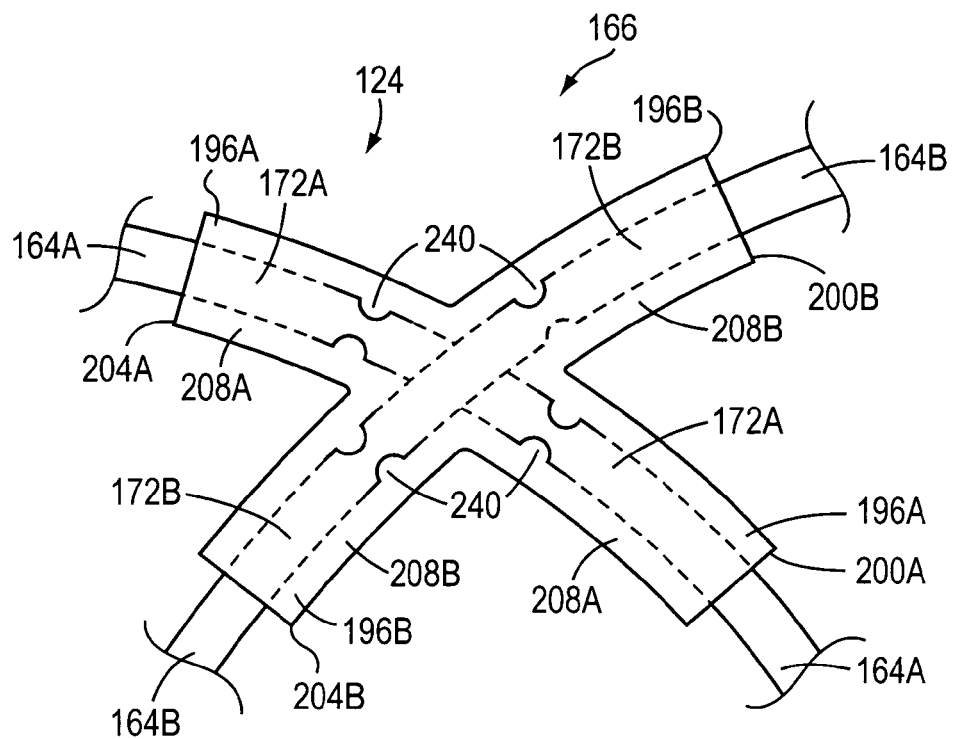
FIG. 7 is a schematic perspective view of a distal end of a retrieval basket according to another illustrative embodiment of the invention.

FIG. 7 depicts a distal end 166 of a retrieval basket 120, including a retainer 124, according to another illustrative embodiment of the invention. According to one feature of this embodiment, the retainer 124 at the distal end 166 of the retrieval basket 120 includes two tubes 196A, 196B. Alternatively, if the retrieval basket 120 includes more than two legs 164, the retainer 124 may include more than two tubes 196.

Figure 8:
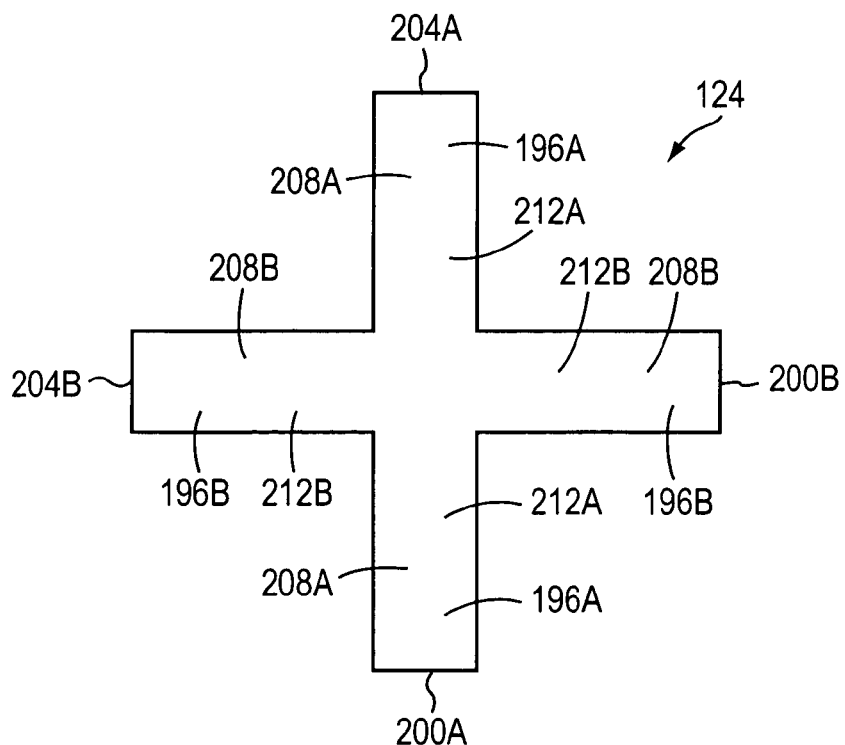
FIG. 8 is a top view of a retainer according to another illustrative embodiment of the invention.

FIG. 8 depicts a retainer 124 according to another illustrative embodiment of the invention. According to the illustrative embodiment, each tube 196A, 196B of the retainer 124 includes a first end 200, a second end 204, and a hollow passageway 208 that extends from the first end 200 to the second end 204. The hollow passageway 208A of the first tube 196A is in fluid communication with the hollow passageway 208B of the second tube 196B. The first tube 196A is offset from the second tube 196B by approximately 90 degrees. The intermediate section 212A of the first tube 196A intersects the intermediate section 212B of the second tube 196B. Accordingly, the retainer 124 is X-shaped.

Referring again to FIG. 7, in one embodiment, a portion of the intermediate portion 172A of the first leg 164A passes through the hollow passageway 208A of the first tube 196A, from its first end 200A to its second end 204A. A portion of the intermediate portion 172B of the second leg 164B passes through the hollow passageway 208B of the second tube 196B, from its first end 200B to its second end 204B. The intermediate portions 172A, 172B of the legs 164A, 164B cross one another at the distal end 166 of the retrieval basket 120.

Figure 9:
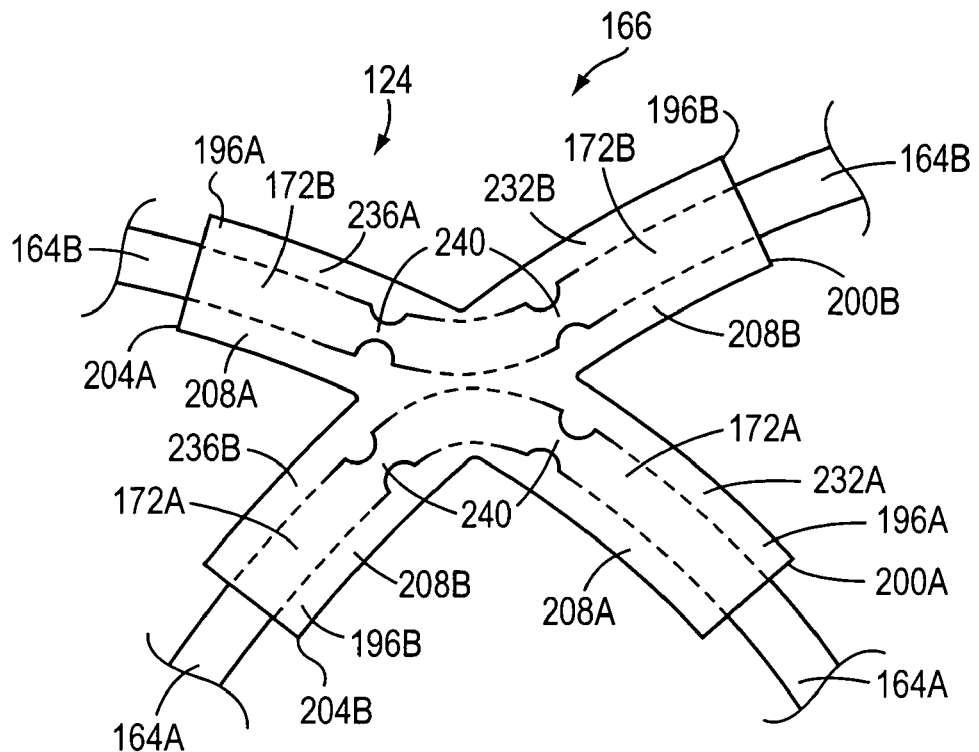
FIG. 9 is a schematic perspective view of a distal end of a retrieval basket according to another illustrative embodiment of the invention.

In an alternative embodiment, referring now to FIG. 9, a portion of the intermediate portion 172A of the first leg 164A passes through both a segment 232A and a segment 236B of the hollow passageways 208A, 208B of the tubes 196A, 196B, respectively. Similarly, the intermediate portion 172B of the second leg 164B passes through both a segment 232B and a segment 236A of the hollow passageways 208B, 208A of the tubes 196B, 196A, respectively. The intermediate portions 172A, 172B of the legs 164A, 164B are side-by-side, but do not cross one another, at the distal end 166 of the retrieval basket 120.

Figure 10:
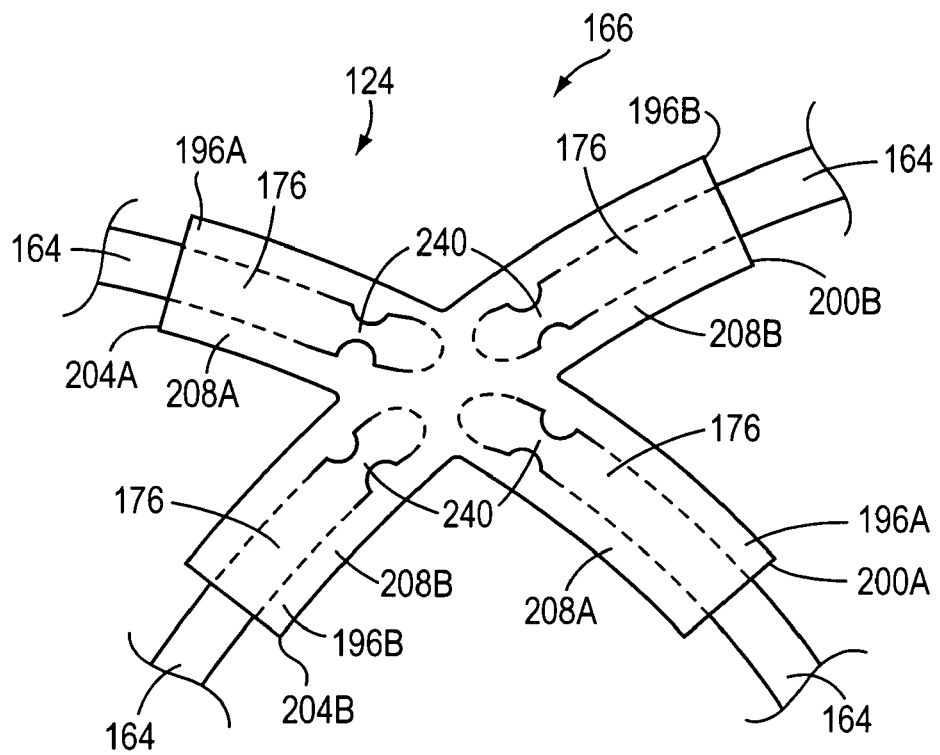
FIG. 10 is a schematic perspective view of a distal end of a retrieval basket according to another illustrative embodiment of the invention.

In yet another embodiment, referring now to FIG. 10, the second end 176 of each leg 164 is located at the distal end 166 of the retrieval basket 120, rather than at the base 160 of the retrieval basket 120, as described above with reference to FIG. 1. Accordingly, no individual leg 164 forms a loop. In a particular embodiment, the retrieval basket 120 includes four such legs 164. Alternatively, the retrieval basket 120 may include any number of such legs 164. As illustrated, according to this embodiment, the second end 176 of each leg 164 is positioned in a segment of the hollow passageway 208 of one of the tubes 196.

In one embodiment, the tubes 196 are made of a heat shrink material, such as, for example, PTFE or a cross-linked polyolefin. According to another embodiment of the invention, as illustrated in FIGS. 7 and 9, the intermediate portion 172 of each leg 164 includes a modified connecting surface, such as, for example, a notch 240. Alternatively, as illustrated in FIG. 10, the second end 176 of each leg 164 includes the notch 240. Once the legs 164 are placed into the hollow passageways 208 of the tubes 196, as described above, heat is applied to the tubes 196. The heat causes the tubes 196 to shrink around the intermediate portions 172 of the legs 164, or, alternatively, around the second ends 176 of the legs 164. The retainer 124 is thereby secured to the distal end 166 of the retrieval basket 120. The notches 240 in the intermediate portions 172 of the legs 164, or, alternatively, at the second ends 176 of the legs 164, allow the legs 164 to be more securely attached to the retainer 124 at the distal end 166 of the basket 120.

The length of the tubes 196, or, alternatively, the portion of the legs 164 covered by the tubes 196, may be varied to suit a particular clinical application. For example, to provide the retrieval basket 120 with heat resistant and/or laser resistant properties, longer tubes 196 made of a heat shrink material are used to cover greater portions of the legs 164 than is otherwise necessary to join the intermediate portions 172 of the legs 164 together. In other words, to provide the retrieval basket 120 with heat resistant and/or laser resistant properties, the tubes 196, in one embodiment, extend along the length of the legs 164, from the distal end 166 of the retrieval basket 120 substantially towards the proximal end 162 of the retrieval basket 120.

Figure 11:
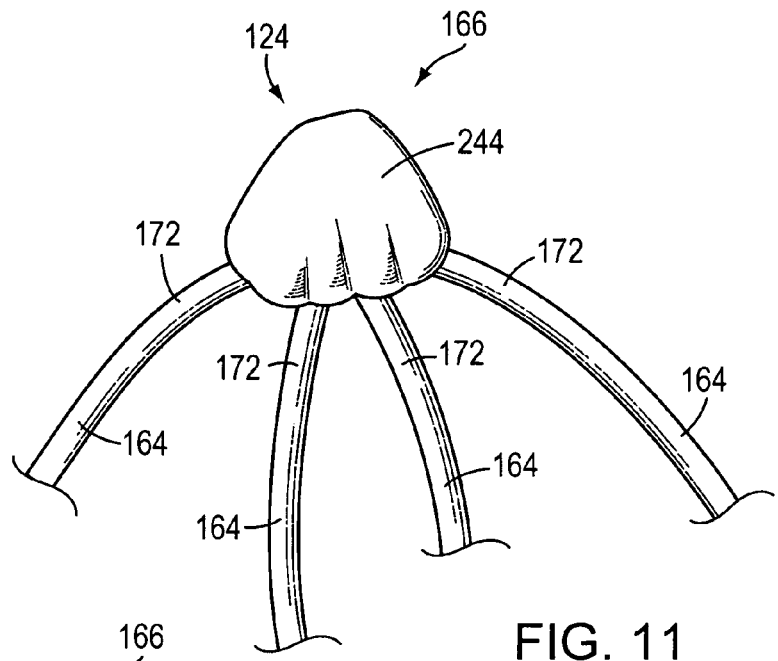
FIG. 11 is a perspective view of a distal end of a retrieval basket according to another illustrative embodiment of the invention.

FIG. 11 depicts a distal end 166 of a retrieval basket 120 according to another illustrative embodiment of the invention. In this embodiment, the retainer 124 at the distal end 166 of the retrieval basket 120 includes a knob 244. In one embodiment, the knob 244 is made from, for example, metals, metal alloys, or polymers. The polymers may include, for example, high density polyethylene (HDPE), nylon, or any other biocompatible thermoplastic. In one embodiment, the knob 244 is injection molded to the intermediate portions 172 of the legs 164 at the distal end 166 of the retrieval basket 120. In another embodiment, the knob 244 is heat shrunk to the intermediate portions 172 of the legs 164 at the distal end 166 of the retrieval basket 120. In yet another embodiment, the knob 244 is an adhesive, such as, for example, a drop of ultra violet curing glue or a drop of cyanoacrylate. The knob 244 is shaped so that it has no outward projections or protrusions that might cause injury or trauma to a patient's tissue.

Figure 12:
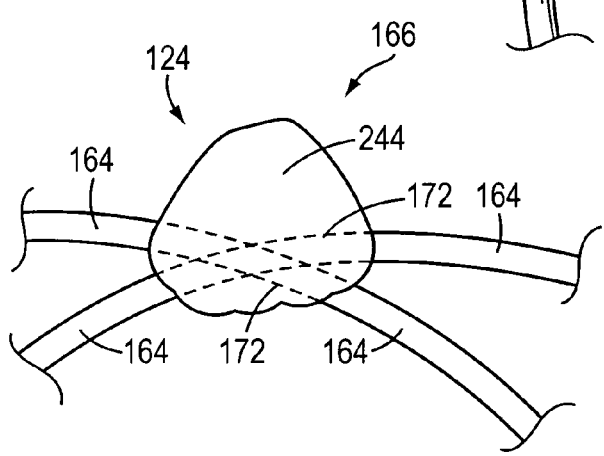
FIG. 12 is a schematic perspective view of the illustrative distal end of the retrieval basket of FIG. 11 according to one embodiment of the invention.
Figure 13:
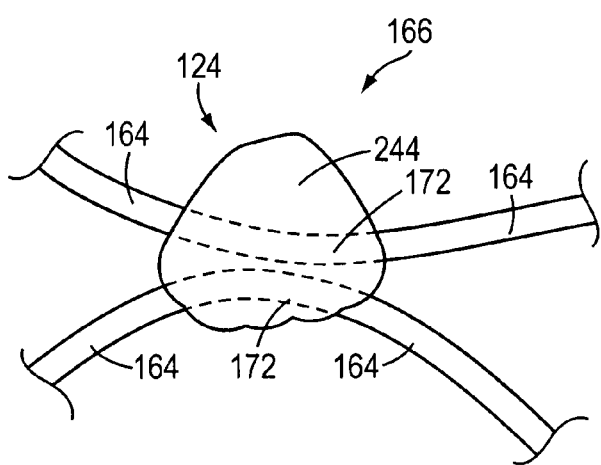
FIG. 13 is a schematic perspective view of the illustrative distal end of the retrieval basket of FIG. 11 according to another embodiment of the invention.

In one embodiment of the knob 244, referring now to FIG. 12, the intermediate portions 172 of the legs 164 are first crossed before the knob 244 is injection molded, heat shrunk, or adhered to the distal end 166 of the retrieval basket 120. Alternatively, as illustrated in FIG. 13, the intermediate portions 172 of the legs 164 are side-by-side, rather than crossing one another, at the distal end 166 of the retrieval basket 120. Accordingly, the distal end 166 of the retrieval basket 120 illustrated in FIG. 13 has a lower profile than the distal end 166 of the retrieval basket 120 illustrated in FIG. 12.

Figure 14:
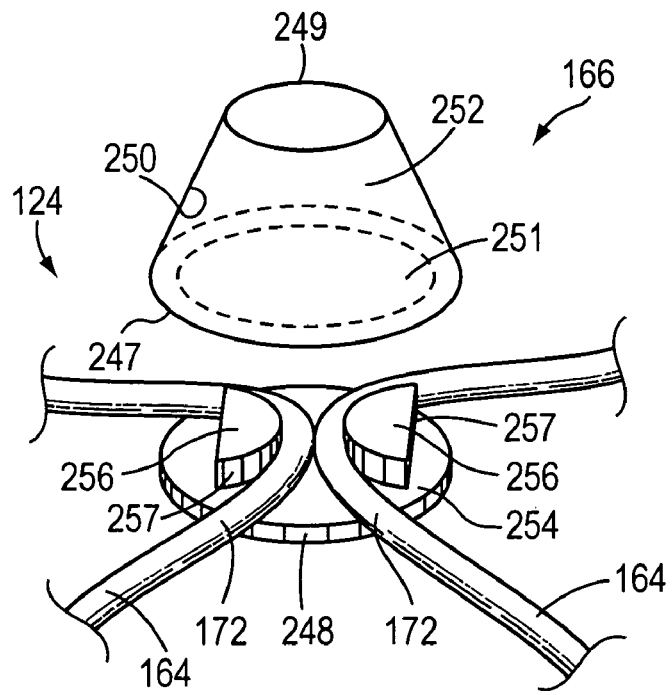
FIG. 14 is a fragmented perspective view of a distal end of a retrieval basket according to another illustrative embodiment of the invention.

FIG. 14 depicts a distal end 166 of a retrieval basket 120 according to another illustrative embodiment of the invention. The retainer 124 at the distal end 166 of the retrieval basket 120 includes a first member 248 and a second member 252. The first and second members 248, 252 may be made, for example, from polymers, such as high density polyethylene (HDPE), nylon, or any other biocompatible theremoplastic. In the embodiment shown, the first member 248 includes an inner face 254 and two risers 256. Alternatively, the first member 248 may include any number of risers 256. A riser 256 is a projection that extends substantially vertically from the inner face 254 of the first member 248. As shown, in one embodiment, the risers 256 are D-shaped with their flat face 257 oriented towards the outside edge of the first member 248 and their rounded face 259 oriented towards the center of the first member 248. In another embodiment, the risers 256 are D-shaped with their rounded face 259 oriented towards the outside edge of the first member 248 and their flat face 257 oriented towards the center of the first member 248. Alternatively, in other embodiments, the risers 256 assume other shapes.

Figure 15:
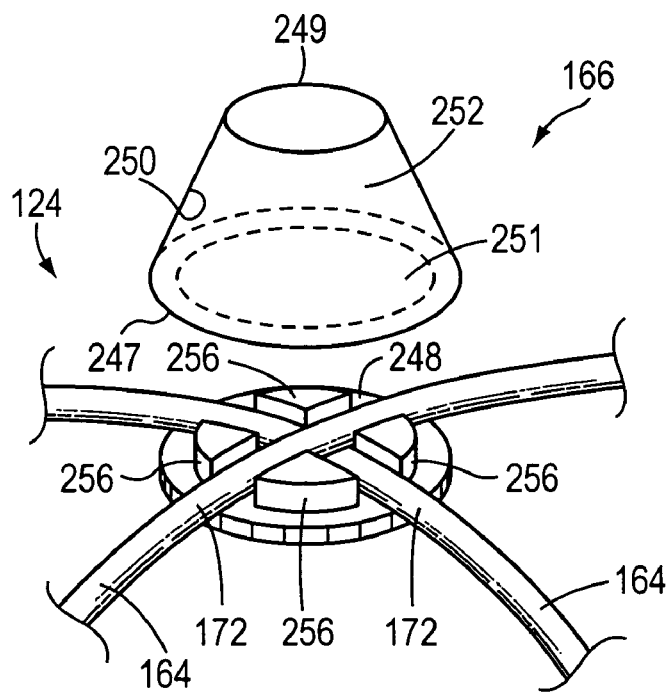
FIG. 15 is a fragmented perspective view of a distal end of a retrieval basket according to another illustrative embodiment of the invention.

To join the intermediate portions 172 of the legs 164 together with the retainer 124 at the distal end 166 of the retrieval basket 120, the intermediate portions 172 of the legs 164 are initially placed across the inner face 254 of the first member 248. For instance, the intermediate portions 172 of the legs 164 may pass between the risers 256. In one embodiment, as illustrated in FIG. 14, the intermediate portions 172 of the legs 164 are side-by-side, but do not cross one another. In another embodiment, referring now to FIG. 15, the intermediate portions 172 of the legs 164 cross one another at the distal end 166 of the retrieval basket 120.

Figure 16:
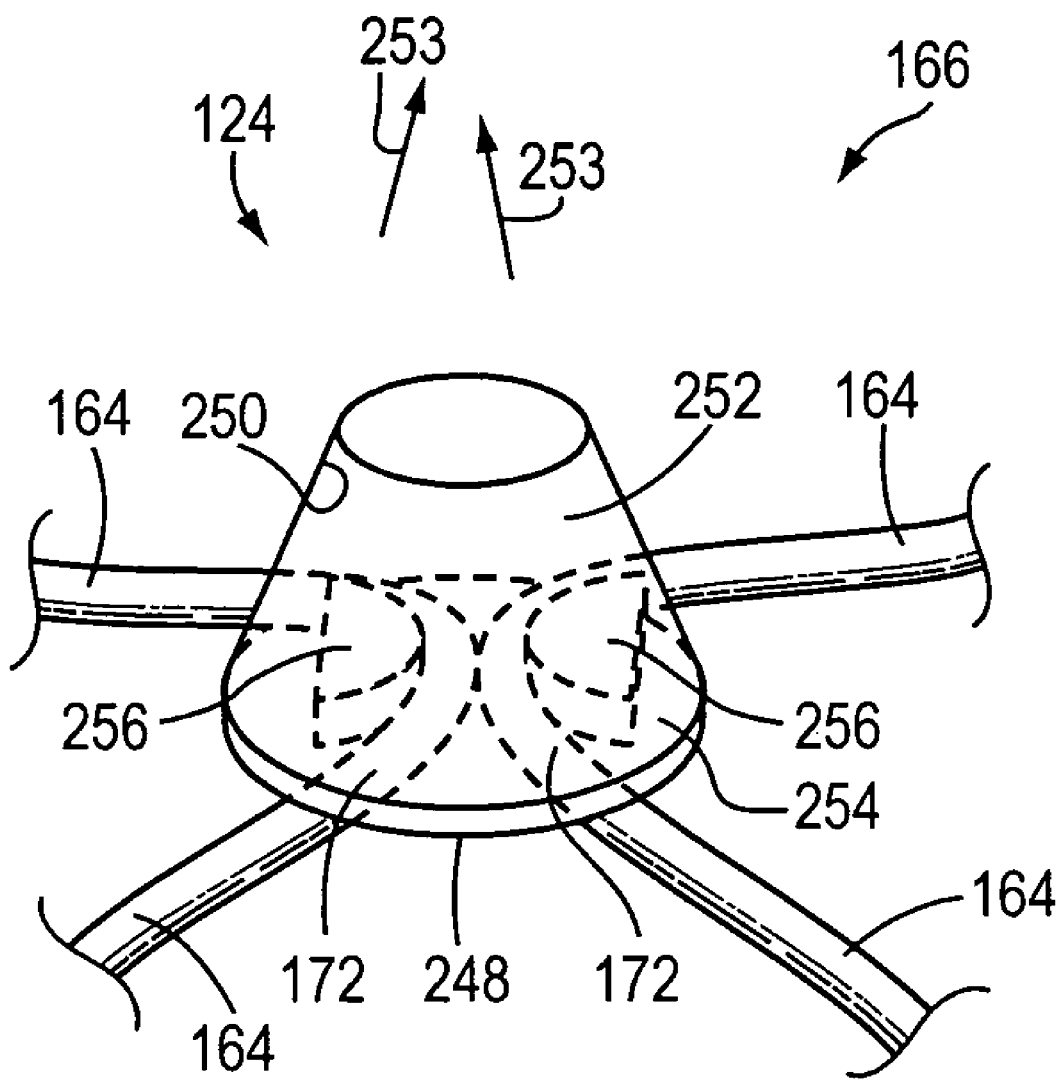
FIG. 16 is a schematic assembled perspective view of the illustrative distal end of the retrieval basket of FIG. 14.

The second member 252 is, in one embodiment, shaped substantially similar to the lower half of a cone. Alternatively, the second member 252 assumes other shapes. The second member 252 includes a first end 247, a second end 249, a lumen 251 that extends at least from the first end 247 towards the second end 249, and an inner surface 250. Following placement of the intermediate portions 172 of the legs 164 on the first member 248, as illustrated in FIG. 14, the second member 252 is attached to the first member 248, as illustrated in FIG. 16. Initially, the risers 256 of the first member 248 contact the inner surface 250 of the second member 252. The risers 256 are forcibly slid along the tapered inner surface 250 of the second member 252 in the direction indicated by arrows 253, thereby providing a force fit between the first member 248 and the second member 252. In one embodiment, an ultrasonic welding horn, for example, then applies ultrasonic vibrations to the first member 248 and to the second member 252. The resulting friction between the risers 256 and the second member 252, caused by the vibrations therebetween, generates heat. As a result, the risers 256 melt and the first member 248 thermally bonds to the second member 252. The intermediate portions 172 of the legs 164 are, therefore, firmly encapsulated between the inner face 254 of the first member 248 and the second member 252.

Figure 17:
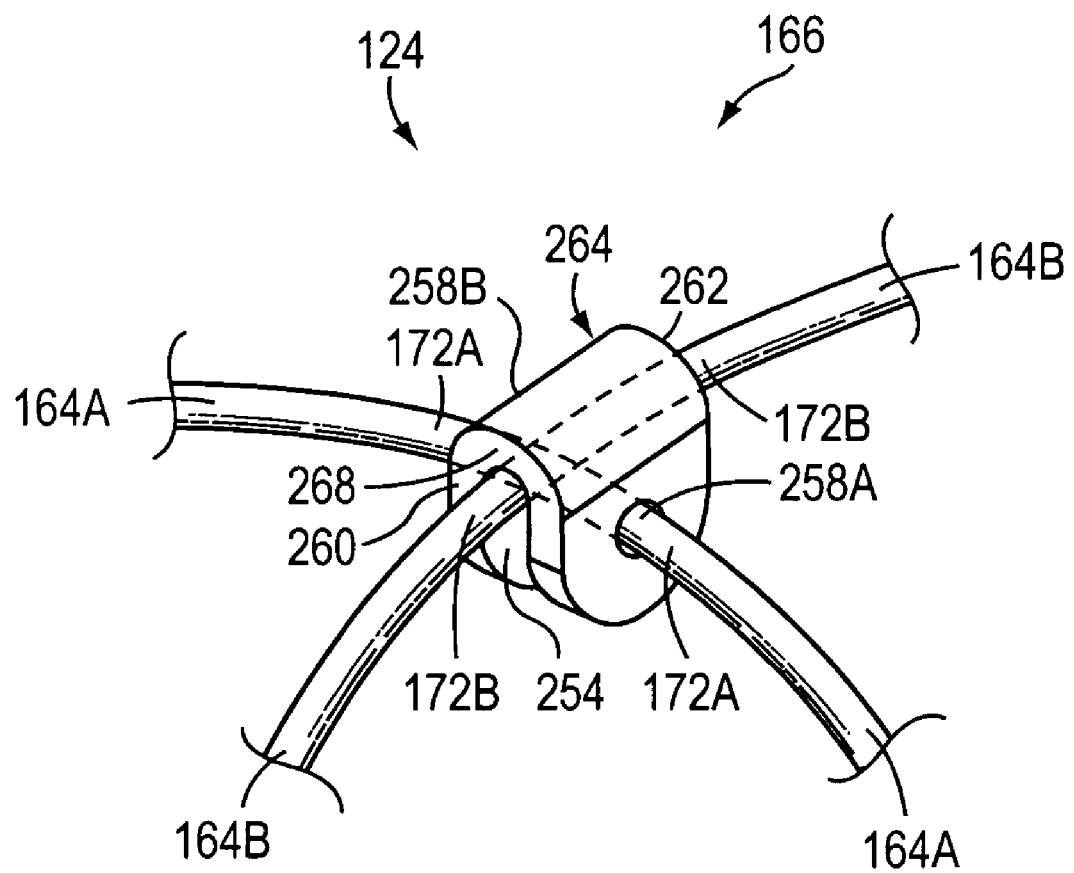
FIG. 17 is a schematic perspective view of a distal end of a retrieval basket according to another illustrative embodiment of the invention.
Figure 18:
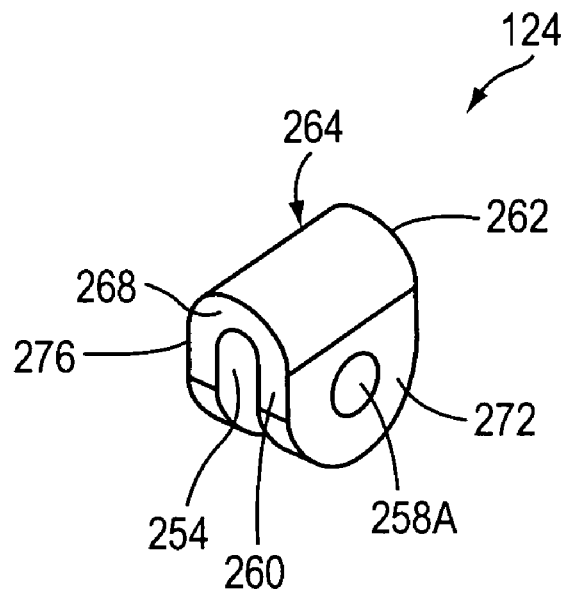
FIG. 18 is a perspective view of a retainer according to another illustrative embodiment of the invention.
Figure 19:
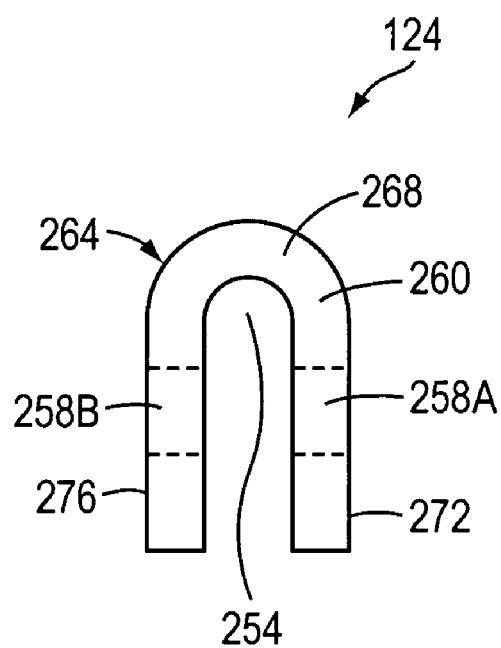
FIG. 19 is an end view of the illustrative retainer of FIG. 18.

FIG. 17 depicts a distal end 166 of a retrieval basket 120 according to another illustrative embodiment of the invention. According to this embodiment, the retainer 124 at the distal end 166 of the retrieval basket 120 includes a lumen 254 and a plurality of openings 258 in fluid communication with the lumen 254. The lumen 254 extends from a first end 260 of the retainer 124 to a second end 262 of the retainer 124, and may or may not be completely enclosed axially on all sides. In one embodiment, the retainer 124 is arch-shaped, and the lumen 254 is defined by an arch-shaped wall 264. Referring now to FIGS. 18 and 19, the wall 264 includes a roof 268, a first surface 272, and a second surface 276. The lumen 254 is open on one side of the retainer 124, i.e. on the side opposite to the roof 268. The first surface 272 includes a first opening 258A, and the second surface 276 includes a second opening 268B. Both openings 258A, 258B are in fluid communication with the lumen 254. The retainer 124 may be made of any kind of biocompatible metal, such as, for example, 300 series or 400 series stainless steels. Alternatively, the retainer 124 may be made of biocompatible thermoplastic.

In one embodiment, referring again to FIG. 17, the intermediate portion 172A of the first leg 164A is positioned in the first opening 258A, passes transversely through the lumen 254, and is positioned in the second opening 258B. The intermediate portion 172B of the second leg 164B is axially positioned in the lumen 254, from at least the first end 260 to at least the second end 262 of the retainer 124. The intermediate portion 172B of the second leg 164B is positioned in the space between the first leg 164A and the roof 268. The intermediate portions 172 of the legs 164 therefore cross one another at the distal end 166 of the retrieval basket 120.

Figure 20:
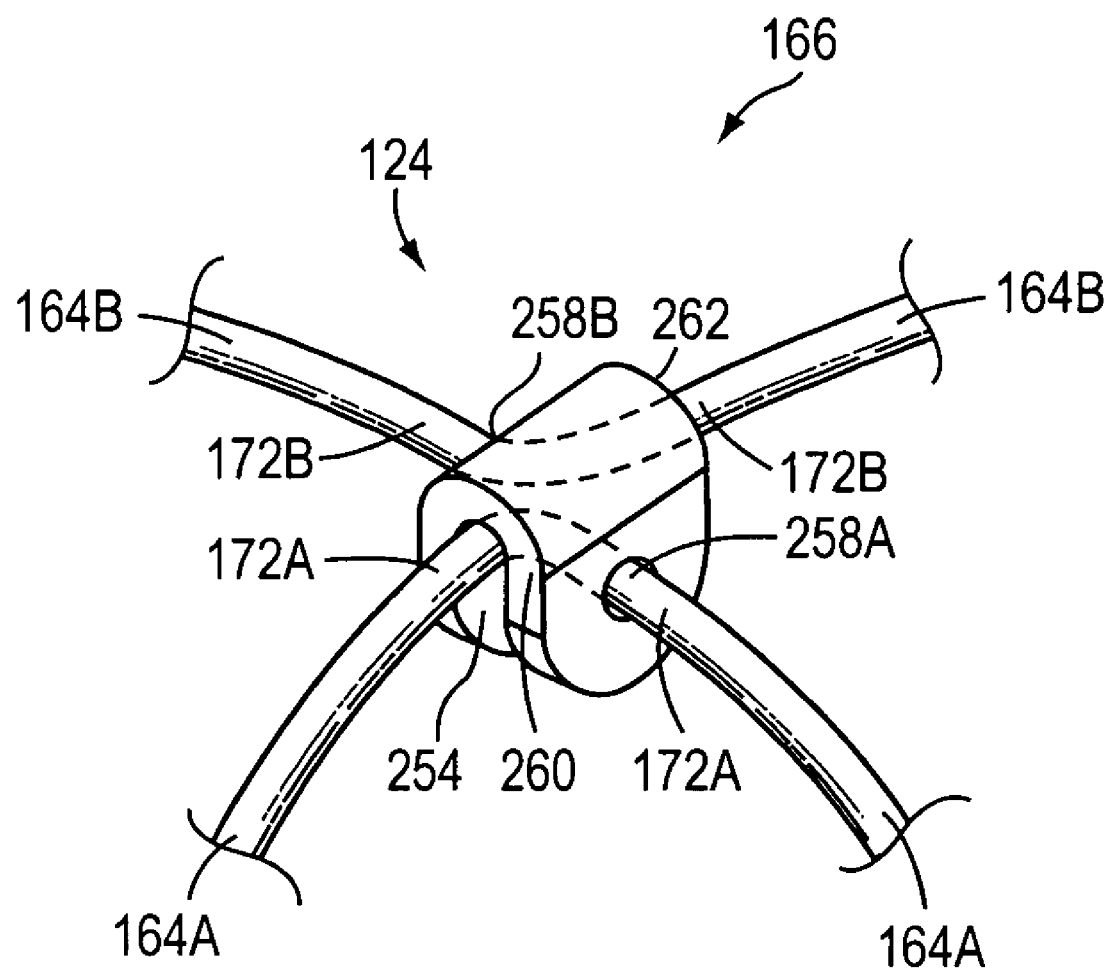
FIG. 20 is a schematic perspective view of a distal end of a retrieval basket according to another illustrative embodiment of the invention.

Alternatively, in another embodiment, and with reference now to FIG. 20, the intermediate portion 172A of the first leg 164A is positioned in the first opening 258A and exits the first end 260 of the retainer 124 through the lumen 254. The intermediate portion 172B of the second leg 164B is positioned in the second opening 258B and exits the second end 262 of the retainer 124 through the lumen 254. As such, the legs 164 are side-by-side, but do not cross one another, at the distal end 166 of the retrieval basket 120.

Figure 21:
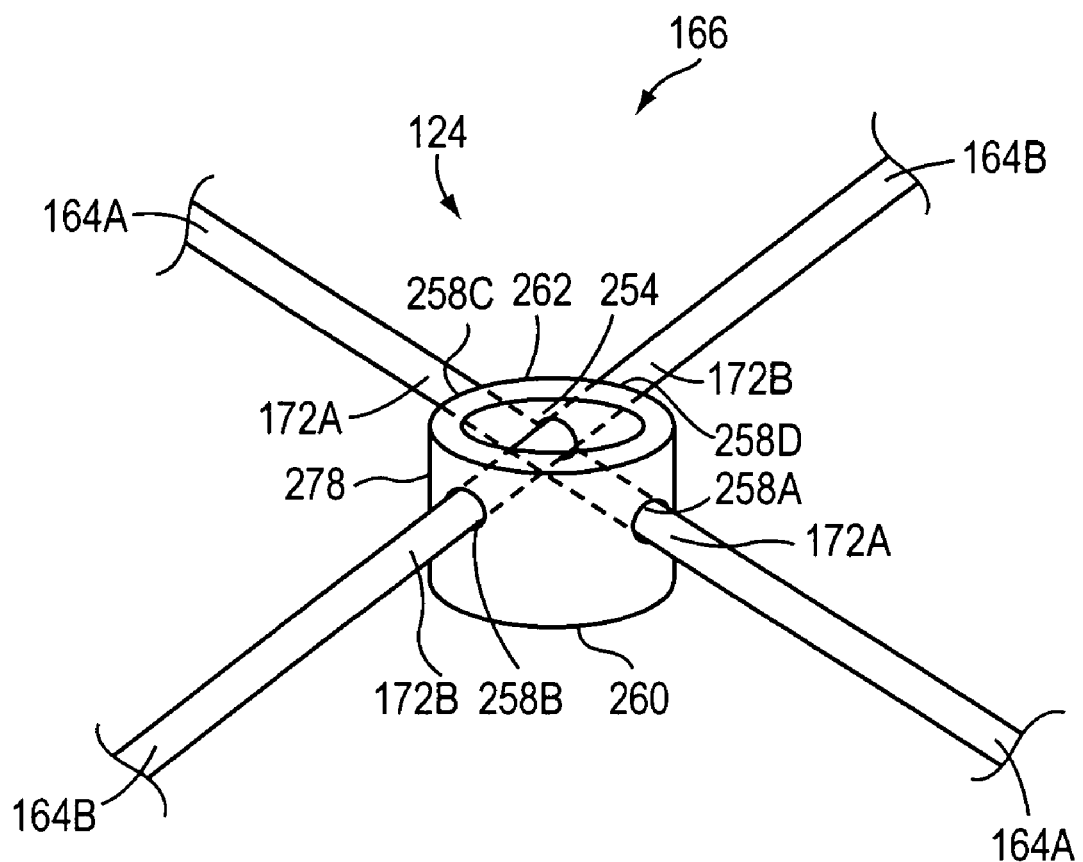
FIG. 21 is a schematic perspective view of a distal end of a retrieval basket according to another illustrative embodiment of the invention.
Figure 22:
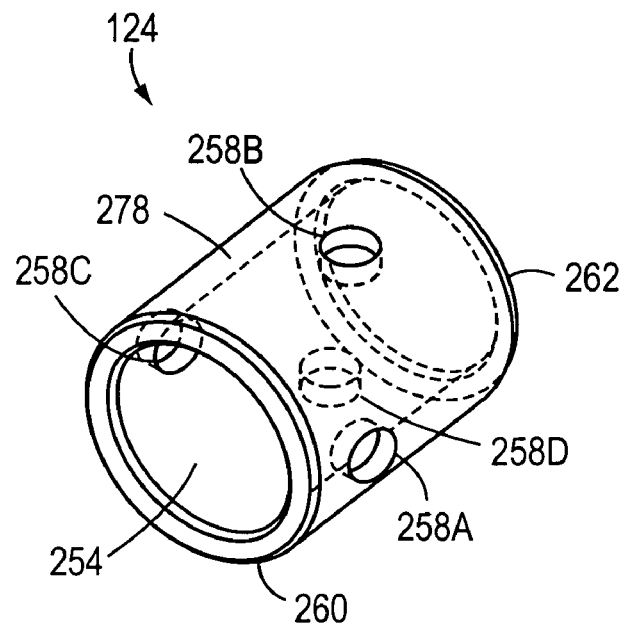
FIG. 22 is a schematic perspective view of a retainer according to another illustrative embodiment of the invention.
Figure 23:
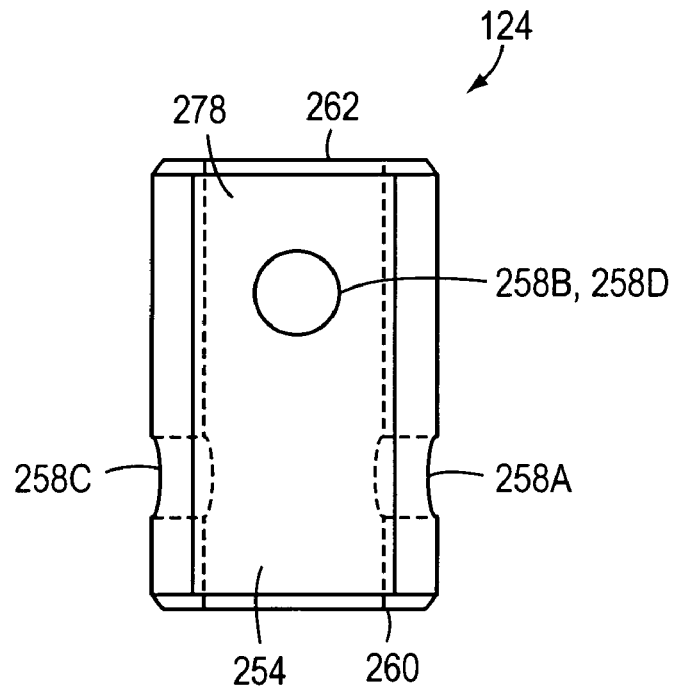
FIG. 23 is a schematic side view of the illustrative retainer of FIG. 22.

FIG. 21 depicts a distal end 166 of a retrieval basket 120 according to another illustrative embodiment of the invention. As shown, and with reference also to FIGS. 22 and 23, the retainer 124 at the distal end 166 of the retrieval basket 120 is cylindrical. The retainer 124 includes a cylinder wall 278 and a lumen 254, extending from a first end 260 to a second end 262 of the cylindrical retainer 124. A plurality of openings 258 in the cylinder wall 278 extend from the exterior surface of the cylinder wall 278 through the cylinder wall 278, and are in fluid communication with the lumen 254 of the retainer 124. For example, the retainer 124 includes four openings 258A-, 258B, 258C, and 258D disposed in the cylinder wall 278 of the retainer 124, positioned approximately 90 degrees apart from one another. The four openings 258A, 258B, 258C, and 258D are in fluid communication with the lumen 254 of the retainer 124. According to this embodiment of the invention, the retainer 124 may be made of any kind of biocompatible metal, such as, for example, 300 series or 400 series stainless steels. Alternatively, the retainer 124 may be made of biocompatible thermoplastic.

According to one feature of this embodiment of the invention, referring again to FIG. 21, the intermediate portion 172A of the first leg 164A is positioned in the first opening 258A, passes transversely through the lumen 254, and is positioned in the third opening 258C. The intermediate portion 172B of the second leg 164B is positioned in the second opening 258B, passes transversely through the lumen 280, and is positioned in the fourth opening 258D. The intermediate portions 172 of the legs 164 cross one another at the distal end 166 of the retrieval basket 120.

Figure 24:
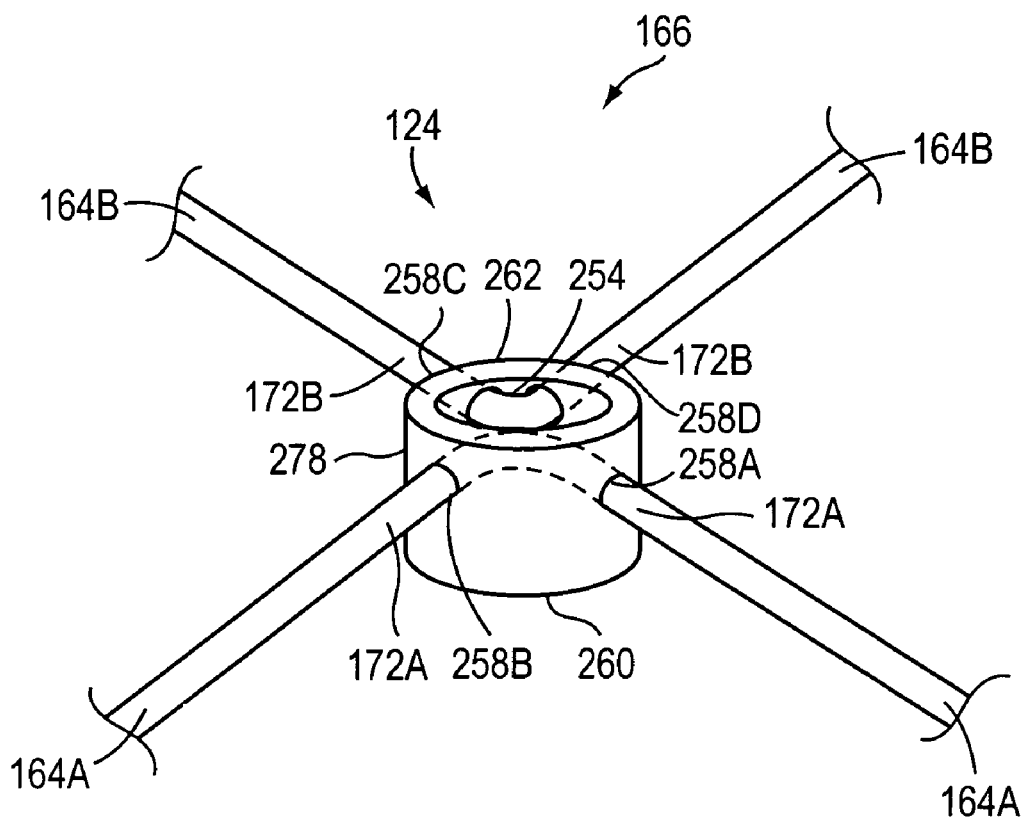
FIG. 24 is a schematic perspective view of a distal end of a retrieval basket according to another illustrative embodiment of the invention.

Alternatively, in another embodiment, and with reference now to FIG. 24, the intermediate portion 172A of the first leg 164A is positioned in the first opening 258A and the second opening 258B of the retainer 124. The intermediate portion 172B of the second leg 164B is positioned in the third opening 258C and the fourth opening 258D of the retainer 124. As illustrated, the legs 164A, 164B are side-by-side, but do not cross one another, at the distal end 166 of the retrieval basket 120.

Further, in one embodiment, the cylindrical retainer 124 is swaged or crimped to tighten down on the intermediate portions 172 of the legs 164.

In another aspect, the invention relates to a method for retrieving biological or foreign material from a body, such as, for example, a body tract or a body canal, with the medical device 100 according to the invention. As described above, the retrieval basket 120 of the device 100 has an atraumatic distal end 166 and allows for the capture of material that is located in difficult-to-access areas within the body. Specifically, because the distal end 166 of the retrieval basket 120 is atraumatic, it can make intimate contact with the surface of the patient's tissue and retrieve materials that are otherwise unrecoverable with conventional tipped baskets.

Figure 25:
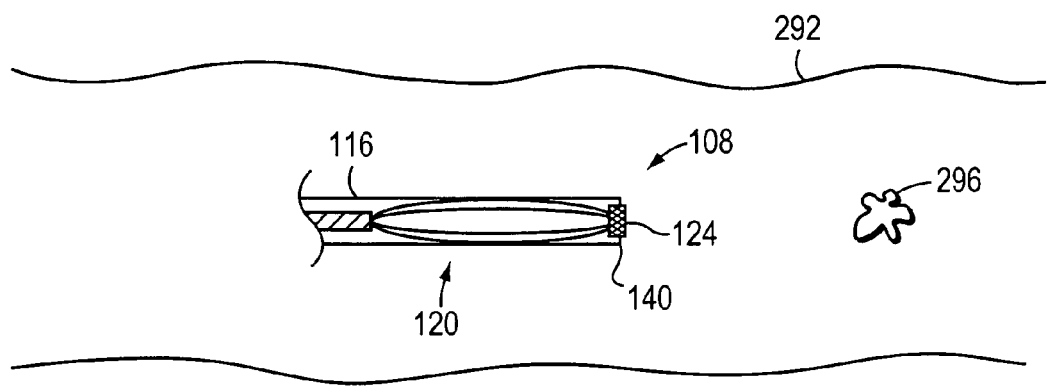
FIGS. 25-28 illustrate the steps in a clinical application of the medical device according to an illustrative embodiment of the invention.
Figure 26:
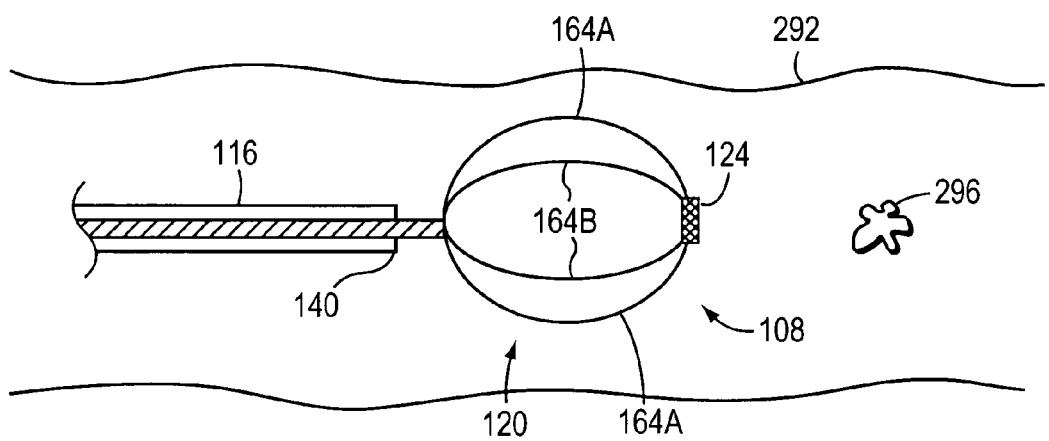
Figure 27:
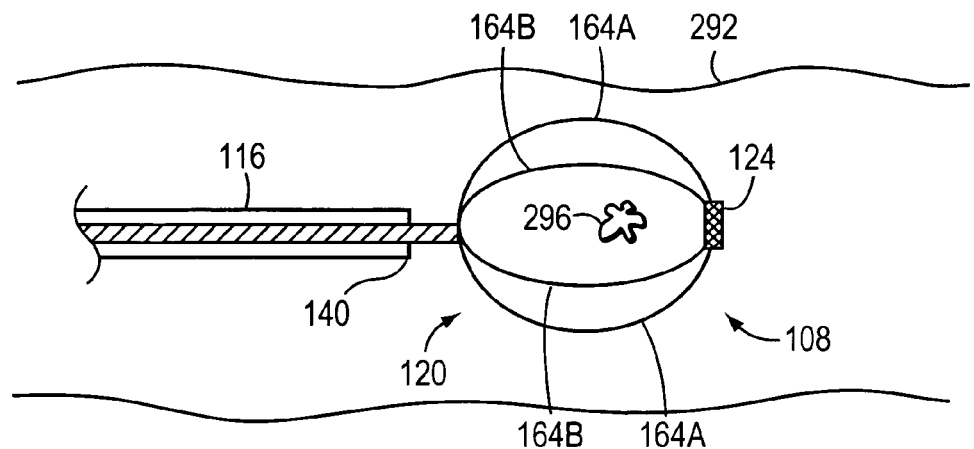
Figure 28:
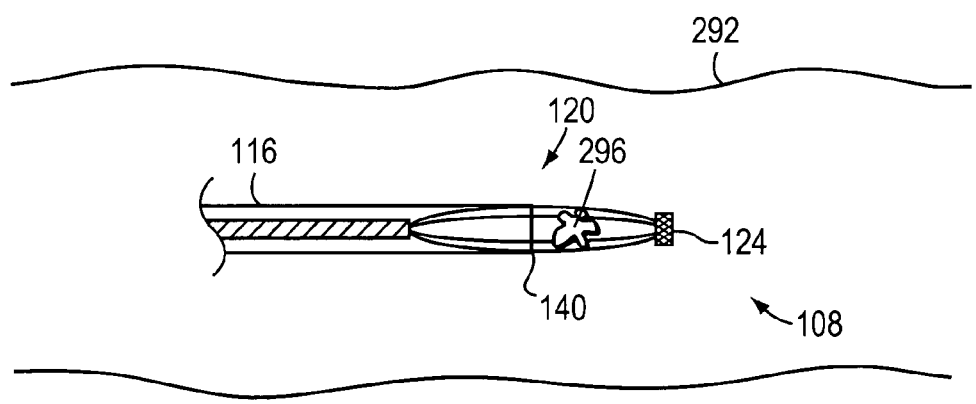

In one embodiment, as shown in FIG. 25, an operator inserts at least the distal end 108 of the medical device 100 into a body tract or a body canal 292 (e.g., the urethra) of a patient where the material 296 to be manipulated, such as a calculus, for example, is located. The operator inserts the medical device 100 into the body tract 292 with the retrieval basket 120 collapsed within the sheath 116. The distal end 140 of the sheath 116 is advanced into the body tract 292 until it is positioned near the material 296. Referring now to FIG. 26, the operator extends the legs 164 of the retrieval basket 120, as discussed above, from the distal end 140 of the sheath 116. Accordingly, the retrieval basket 120 achieves the expanded position. The operator maneuvers the retrieval basket 120 via the handle 112, which is located outside of the patient's body, until the retrieval basket 120 entraps the material 296, as shown in FIG. 27. Referring now to FIG. 28, the operator secures the material 296 within the retrieval basket 120 by moving the retrieval basket 120 relative to the sheath 116 to close the legs 164 of the retrieval basket 120 around the material 296, as described above. With the material 296 so gripped or held by the retrieval basket 120, the medical device 100 and the material 296 are removed from the patient's body. Specifically, the operator withdraws the medical device 100 from the body along the same path originally used to advance the medical device 100 into the body. Optionally, before the medical device 100 is withdrawn from the patient's body with the captured material 296, the material 296 may be broken apart by, for example, laser energy or lithotripsy. Mechanisms for breaking up the material 296 before its removal from the body may be part of the medical device 100 or they may be separate tools/devices that are also inserted into the body and utilized at the appropriate time during the procedure of removing the material 296.

The material 296 that may be captured with the medical device 100 according to the invention includes any biological or foreign material. For example, the material 296 may be a kidney stone, a ureteral stone, a urethral stone, a urinary bladder stone, a gallbladder stone, or a stone in the biliary tree. The medical device 100 according to the invention may also be used to trap, immobilize, sweep, and/or release materials within the body of a patient.

Variations, modifications, and other implementations of what is described herein will occur to those of ordinary skill in the art without departing from the spirit and the scope of the invention. The invention is not to be defined only by the preceding illustrative description.

What is claimed is:

1. A medical device, comprising:
   a handle;
   a sheath joined to the handle, the sheath comprising a lumen;
   a retrieval basket comprising a proximal end, a distal end, and a plurality of legs, each of the plurality of legs being a continuous loop from a first end to a second end and having an intermediate portion, wherein the first and second ends of the plurality of legs are located at the proximal end of the retrieval basket and the intermediate portion of each of the plurality of legs is located between the first and second ends of the leg, the intermediate portion being positioned at the distal end of the retrieval basket, the retrieval basket achieving a collapsed position when restrained in the lumen of the sheath and an expanded position when unrestrained by the lumen of the sheath; and
   a retainer coupled to the distal end of the retrieval basket to secure at least the intermediate portion of one of the plurality of legs to the intermediate portion of another of the plurality of legs, wherein the intermediate portion of each of the plurality of legs includes a notch, wherein at least the intermediate portion of one of the plurality of legs crosses over the intermediate portion of another of the plurality of legs within the retainer, wherein the retainer comprises a plurality of tubes having a substantially constant outer diameter and each defining a hollow passageway, wherein an inner surface of each hollow passageway attaches to the notch of a corresponding one of the plurality of legs, and wherein the hollow passageway of one of the plurality of tubes intersects the hollow passageway of another of the plurality of tubes.

2. The medical device of claim 1 wherein the retainer is X-shaped.

3. The medical device of claim 1 wherein each of the plurality of tubes comprises a first end, and a second end, and the hollow passageway extends from the first end to the second end.

4. The medical device of claim 3 wherein at least the hollow passageway of one of the plurality of tubes is in fluid communication with the hollow passageway of another of the plurality of tubes.

5. The medical device of claim 3 wherein the plurality of tubes comprise heat shrink material.

6. The medical device of claim 1 wherein each tube is substantially perpendicular to at least one other tube.

7. The medical device of claim 1 wherein each of the plurality of tubes of the retainer extends along a length of the legs substantially to a proximal end of the retrieval basket.

8. A method of retrieving a material from a body, comprising:
   inserting a medical device into the body, the medical device comprising:
      a handle;
      a sheath joined to the handle, the sheath comprising a lumen;
      a retrieval basket comprising a proximal end, a distal end, and a plurality of legs, each of the plurality of legs being a continuous loop from a first end to a second end and having an intermediate portion, wherein the first and second ends of the plurality of legs are located at the proximal end of the retrieval basket and the intermediate portion of each of the plurality of legs is located between the first and second ends of the leg, the intermediate portion being positioned at the distal end of the retrieval basket, the retrieval basket achieving a collapsed position when restrained in the lumen of the sheath and an expanded position when unrestrained by the lumen of the sheath; and
      a retainer coupled to the distal end of the retrieval basket to secure at least the intermediate portion of one of the plurality of legs to the intermediate portion of another of the plurality of legs, wherein the intermediate portion of each of the legs includes a notch, wherein at least the intermediate portion of one of the plurality of legs crosses over the intermediate portion of another of the plurality of legs within the retainer, wherein the retainer comprises a plurality of tubes having a substantially constant outer diameter and each defining a hollow passageway, wherein an inner surface of each hollow passageway attaches to the notch of a corresponding one of the plurality of legs, and wherein the hollow passageway of one of the plurality of tubes intersects the hollow passageway of another of the plurality of tubes;
   positioning the retrieval basket proximate to the material to be retrieved with the retrieval basket in the expanded position;
   capturing the material with the retrieval basket; and
   withdrawing the retrieval basket from the body to remove the captured material from the body.

9. The method of claim 8 wherein each tube is substantially perpendicular to at least one other tube.

10. The method of claim 8 wherein each of the plurality of tubes of the retainer extends along a length of the legs substantially to a proximal end of the retrieval basket.

11. A medical device, comprising:
    a handle;
    a sheath joined to the handle, the sheath comprising a lumen;
    a retrieval basket comprising a proximal end, a distal end, and a plurality of legs, each of the plurality of legs being a continuous loop from a first end to a second end and having an intermediate portion, wherein the first and second ends of the plurality of legs are located at the proximal end of the retrieval basket and the intermediate portion of each of the plurality of legs is located between the first and second ends of the leg, the intermediate portion being positioned at the distal end of the retrieval basket, the retrieval basket achieving a collapsed position when restrained in the lumen of the sheath and an expanded position when unrestrained by the lumen of the sheath; and
    a retainer including a plurality of tubes and coupled to the distal end of the retrieval basket to secure at least the intermediate portion of one of the plurality of legs to the intermediate portion of another of the plurality of legs, wherein at least the intermediate portion of one of the plurality of legs crosses over the intermediate portion of another of the plurality of legs within the retainer, wherein the intermediate portion of the one of the plurality of legs comprises a connecting surface modified relative to adjacent surfaces of the intermediate portion of the one of the plurality of legs, wherein the connecting surface comprises at least one notch; wherein an inner surface of each of the plurality of tubes attaches to the connecting surface of a corresponding one of the plurality of legs, and wherein each of the plurality of tubes of the retainer includes a substantially constant outer diameter.

12. The medical device of claim 11 wherein each of the plurality of tubes defines a hollow passageway.

13. The medical device of claim 12 wherein the hollow passageway of one of the plurality of tubes intersects the hollow passageway of another of the plurality of tubes.

14. The medical device of claim 12 wherein at least the hollow passageway of one of the plurality of tubes is in fluid communication with the hollow passageway of another of the plurality of tubes.

15. The medical device of claim 12 wherein the plurality of tubes comprises heat shrink material.

16. The medical device of claim 11 wherein each tube is substantially perpendicular to at least one other tube.

17. The medical device of claim 11 wherein each of the plurality of tubes of the retainer extends along a length of the legs substantially to a proximal end of the retrieval basket.

* * * * *